(12) United States Patent
Vanhamel et al.

(10) Patent No.: US 7,160,590 B2
(45) Date of Patent: Jan. 9, 2007

(54) PACKAGING INCLUDING A COMPOSITE WEB COMPRISING POROUS LAYER

(75) Inventors: Steven Vanhamel, Herk-de-Stad (BE); Thomas Claes, Hasselt (BE)

(73) Assignee: Advanced Technology Materials, Inc., Danbury, CT (US)

( * ) Notice: Subject to any disclaimer, the term of this patent is extended or adjusted under 35 U.S.C. 154(b) by 20 days.

(21) Appl. No.: 10/643,026

(22) Filed: Aug. 18, 2003

(65) Prior Publication Data

US 2005/0042398 A1 Feb. 24, 2005

(51) Int. Cl.
- A61B 17/06 (2006.01)
- A61B 19/02 (2006.01)
- B65D 51/18 (2006.01)
- B65D 43/02 (2006.01)
- B65D 33/01 (2006.01)
- G01M 3/04 (2006.01)
- G01M 3/32 (2006.01)
- G01M 3/36 (2006.01)

(52) U.S. Cl. .............. 428/35.7; 428/34.3; 428/35.2; 428/36.1; 428/36.2; 428/36.5; 206/363; 206/364; 206/365; 206/366; 206/368; 206/369; 206/370; 206/439; 206/484.1; 206/484.2; 220/254.1; 220/257.1; 215/251; 383/102; 383/111; 422/102; 73/40.7; 73/45.4; 73/52

(58) Field of Classification Search .............. 428/34.3, 428/35.2, 35.7, 36.1, 36.2, 36.5, 511, 513; 206/363–370, 439, 484.1, 484.2; 220/254.1, 220/257.1; 215/251; 383/101, 102, 111, 383/113; 422/102; 73/49.3, 52, 40, 40.7, 73/45.4, 70.7

See application file for complete search history.

(56) References Cited

U.S. PATENT DOCUMENTS

| 4,055,672 | A | * | 10/1977 | Hirsch et al. ............... 426/127 |
| 4,461,420 | A | * | 7/1984 | Horvath ..................... 229/120 |
| 4,539,836 | A | * | 9/1985 | Hester et al. ................ 73/49.3 |
| 5,217,772 | A | * | 6/1993 | Brown et al. .............. 428/41.3 |
| 5,418,022 | A | * | 5/1995 | Anderson et al. .......... 428/35.2 |
| 5,459,978 | A | * | 10/1995 | Weiss et al. .................. 53/425 |
| 5,591,468 | A | * | 1/1997 | Stockley et al. ............ 426/106 |
| 5,976,299 | A |   | 11/1999 | Ivey .......................... 156/270 |
| 6,065,597 | A | * | 5/2000 | Pettersson et al. ......... 206/364 |
| 6,251,489 | B1 | * | 6/2001 | Weiss et al. ............... 428/35.2 |
| 6,460,405 | B1 | * | 10/2002 | Mayer et al. ................ 73/40.7 |
| 6,513,366 | B1 |   | 2/2003 | Stauffer |
| 2003/0015021 | A1 | * | 1/2003 | Mayer et al. ................ 73/40.7 |

* cited by examiner

Primary Examiner—Rena Dye
Assistant Examiner—Chris Bruenjes
(74) Attorney, Agent, or Firm—Vincent K. Gustafson; Intellectual Property Technology Law; David M. Shofi

(57) ABSTRACT

A multilayer web article, including a first layer of a porous material, e.g., Tyvek® film, and a second layer overlying and sealed to the first layer. The second layer is non-porous to passage of gas therethrough and includes a peelable film, e.g., of polyethylene, in contact with the first layer of porous material. The peelable film permits peeling removal of the second layer from the first layer to expose the first layer of porous material for passage of gas therethrough. In a specific construction, the web article constitutes one of oppposedly facing panels of a lay-flat bag article, in which the facing panels are bonded to one another along superposed edges thereof. After pressurization integrity testing of the bag, the peelable film is peeled away to enable steam - and/or ETO-sterilization of the bag and its contents to be carried out.

42 Claims, 2 Drawing Sheets

PACKAGING INCLUDING A COMPOSITE WEB COMPRISING POROUS LAYER

FIELD OF THE INVENTION

The present invention relates to composite webs, packaging including such composite webs, and integrity testing of packaging that includes a porous web structural component.

DESCRIPTION OF THE RELATED ART

Many products are packaged in composite packaging that must accommodate sterilization procedures to render the packaged product suitable for its ultimate use. Examples of such products include medical devices that contact the body or body fluids in ultimate use, pharmaceutical therapeutic agents that are packaged for subsequent dispensing, and food and chemicals that are susceptible to degradation and deterioration if contaminated by microbiological agents.

A variety of sterilization procedures have come into use for rendering such packaged products free of deleterious contaminants. Among these sterilization procedures, sterilization by exposure of the package to steam and/or ethylene oxide (ETO) is often employed as a reliable and safe methodology for sterilization of bags and similar containment structures that include gas-porous and non-porous portions. For example, steam- and/or ETO-sterilizable bags commonly have one side that is porous for the sterilant gas and provides a microbiological barrier to maintain the sterilization of the packaged contents after exposure to the sterilant gas, and a second side that is non-porous to the sterilant gas. The porous side of such containers is typically paper or a flash-spun and bonded polymer film, such as Tyvek® film (commercially available from E.I. DuPont de Nemours & Co., Wilmington, Del.). Tyvek® film is formed from high density polyethylene fibers that are flash spun and then laid as a web on a moving bed for consolidation by heat and pressure to form the product sheet-form material, and is a preferred form of porous packaging material for many applications due to its penetration resistance to bacteria, tear strength and puncture-resistant character.

The porous films of such packaging, however, whether paper or synthetic resin-based, have the associated deficiency that they do not permit non-destructive testing of their integrity. In many applications, such as the use of isolator bags that maintain physical separation of product components, purchasers typically desire each bag to be individually tested for seal integrity.

When Tyvek® film is used for fabricating such bags, seal integrity can only be carried out by leak testing using a colorimetric fluid such as methylene blue liquid, which however renders the bag unsuitable for subsequent use. In other packaging material applications, bags are typically subjected to non-destructive pressure testing, in which the bag is filled with compressed air, and pressure loss as a function of time is then monitored to verify fluid-tightness of the bag and integrity of its seams and surfaces. Due to the presence of the porous sheet material in the bag, however, this mode of testing cannot be used.

Accordingly, there is a continuing and critical need in the art for improved structures in steam- and/or ETO-sterilizable bags and other containment structures including porous fibrous web sheets, which require integrity testing for qualification for subsequent use.

SUMMARY OF THE INVENTION

The present invention relates to porous web composites, packaging comprising same, and integrity testing of packaging that includes a porous web structural component.

In one aspect, the present invention relates to a multilayer web article, comprising:
a first layer of a porous material; and
a second layer overlying and sealed to the first layer, such second layer (i) being non-porous to passage of gas therethrough and (ii) comprising a peelable film in contact with the first layer of porous material, such peelable film permitting peeling removal of the second layer from the first layer to expose the first layer of porous material for passage of gas therethrough.

In another aspect, the invention relates to a packaging article useful for pressurization integrity testing and after pressurization integrity testing being permeable to sterilant gas for sterile packaging of a product article disposable therein, such packaging article comprising:
a sheet form structural component including: a first layer of a porous material that is permeable to passage of sterilant gas therethrough in exposure to a sterilant gas environment; and a second layer overlying and sealed to the first layer,
said second layer (i) being non-porous to passage of said sterilant gas therethrough and (ii) comprising a peelable film in contact with the first layer of porous material, said peelable film permitting peeling removal of the second layer from the first layer to expose the first layer of porous material for passage of said sterilant gas therethrough.

A still further aspect of the invention relates to a method of integrity testing a packaging article by pressure retention testing and rendering such packaging article permeable to sterilant gas for sterile packaging of a product article therein after such pressure retention testing, and sterilizing the packaging, the method comprising:
(a) fabricating the packaging article with a sheet form structural component including: a first layer of a porous material that is permeable to passage of sterilant gas therethrough in exposure to a sterilant gas environment; and a second layer overlying and sealed to the first layer, wherein the second layer (i) is non-porous to passage of said sterilant gas therethrough and (ii) comprises a peelable film in contact with the first layer of porous material, the peelable film permitting peeling removal of the second layer from the first layer to expose the first layer of porous material for passage of said sterilant gas therethrough;
(b) pressurizing said packaging article by a compressed gas and monitoring pressure retention by the packaging article to determine its integrity;
(c) after completion of step (a) with a verification of said integrity, peelingly removing the second layer from the first layer to expose the first layer of porous material for passage of said sterilant gas therethrough; and
(d) after step (c), exposing said packaging article to said sterilant gas to sterilize said packaging article.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
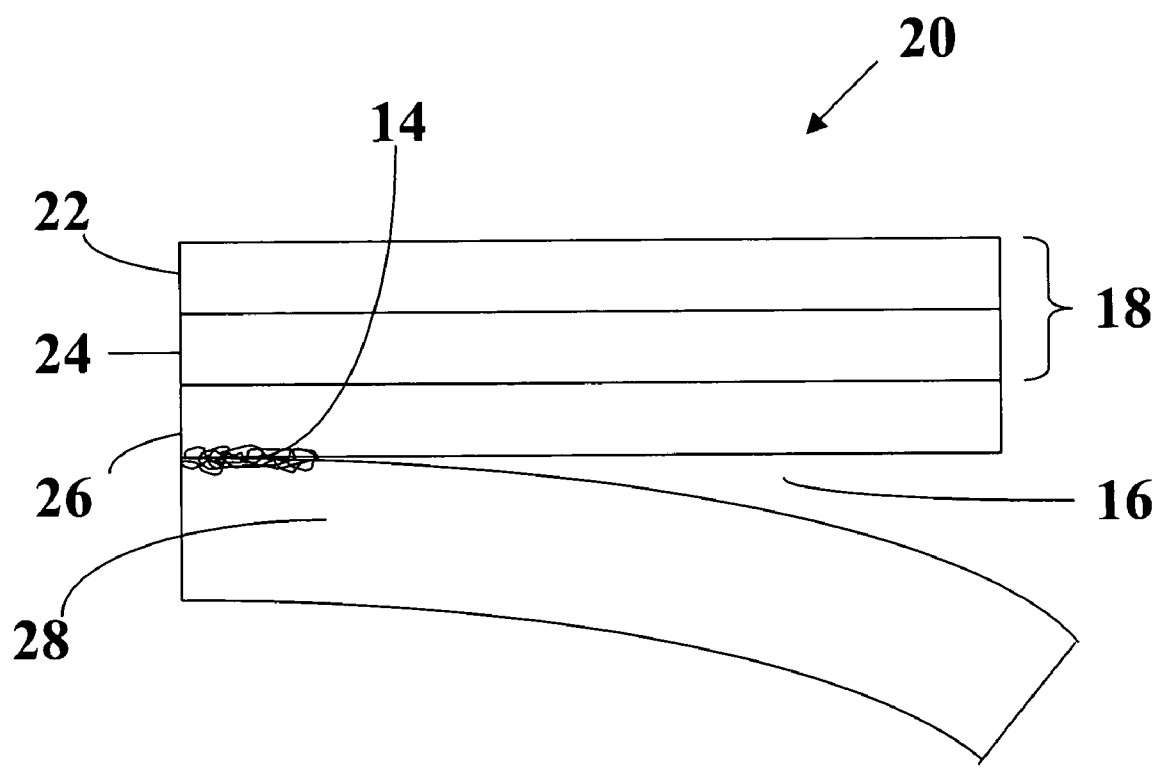
FIG. 1 is a schematic representation of a portion of a package according to one embodiment of the invention, showing the constituent laminae thereof.

The present invention is based on the discovery of a multilaminate construction that is usefully employed in the fabrication of containment structures to accommodate integrity testing and which concurrently allows the package to be formed with a porous sheet that is porous to sterilant gases such as steam or ETO in the sterilization of the package after its fabrication.

More specifically, the invention relates to a composite web article including porous sheet useful for forming packaging that is subjected to sterilant gases after the package is formed, in which the porous sheet has sealed to it an overlying sheet including a peelable polymeric film. The overlying sheet provides a non-porous barrier over the porous sheet. The overlying sheet can be a single layer sheet or it can be of multilayer character, formed for example by coextrusion and including a peelable layer and a non-porous backing layer. If of a single layer sheet construction, the overlying sheet is also non-porous. Regardless of its particular composition, the overlying sheet must be peelable from the porous sheet and must be non-porous in character.

By such construction, the overlying sheet including the peelable polymeric film permits compressed gas fill of the package for integrity testing, and after such testing is completed, the overlying sheet can be readily peelably removed from the underlying porous sheet, to yield the product package having a porous sheet as a structural member thereof. In this manner, the peel-away removal of the overlying sheet "exposes" the underlying porous sheet and facilitates penetration through the porous sheet, e.g., into the interior volume of the package, of sterilant gas such as steam and/or ETO.

In one embodiment, the invention provides a sterilizable bag constructed of a first sheet of a non-porous polymeric film, e.g., polyethylene film, and a facing sheet of a porous material, e.g., a paper (cellulosic web) or synthetic polymeric material, such as Tyvek® polyethylene sheet, with a peelable overlying sheet sealed to an exterior face of the facing sheet of porous material. For example the porous material and non-porous material sheets can be generally coextensive in area and in register with one another, being joined to one another by perimeter seams such as can be formed by thermal bonding, ultrasonic welding, adhesive bonding, or any other suitable technique. The porous sheet can alternatively be a fibrous web of a form analogous to Tyvek® film, but constituted of other synthetic resin polymeric material, e.g., polysulfone, polyinide, polypropylene, polybutylene, polyvinylchloride, polyurethane, polystyrene, etc.

The peelable overlying sheet can be a coextruded sheet including a peel-to-porous sheet layer (that is sealed to the exterior face of the facing sheet of porous material) and a non-porous polymeric layer such as a polyethylene backing layer on the peelable layer. The peelable layer can be formed of any suitable resin material, e.g., of a type that is used in peelable to Tyvek® films used in medical packaging where the peel property is used for opening the pouch or other container.

In this respect, it is to be noted that standard Tyvek® peel pouches the peelable layer thickness and seal temperatures are selected to obtain an opaque seal with a limited seal strength that is typically on the order of 5 Newtons/15 millimeters seal width. In the case of isolator bags or other Tyvek® bags that need integrity testing, the seal strength needs to be substantially higher, e.g., on the order of at least 20–25 Newtons/15 millimeters seal width. Such higher seal strength in turn requires a transparent seal that necessitates higher temperature for sealing. Since the making of the transparent seal requires higher temperatures, the construction of the peelable film must be modified in order to avoid damage to the peel layer. The present invention therefore embodies a substantial departure from the methods of the prior art that have been employed to form standard Tyvek® peel pouches, further evidencing the inventive character of the containment structures and package articles of the present invention.

In the foregoing illustrative embodiment involving a polyethylene film as a non-porous sheet member of the product package, the polyethylene can be of any suitable type, as suitable for steam- and/or ETO-sterilization. In the case of steam sterilization of the product package, the polyethylene is desirably a high density polyethylene (HDPE) material. In the case of sterilization by ETO, the polyethylene can be low density polyethylene (LDPE), linear low density polyethylene (LLDPE), or any other polyethylene. The porous layer of the final product package desirably is a Tyvek® sheet, and the peelable sheet overlying the Tyvek® sheet desirably is a peelable polyethylene sheet.

In this embodiment, the PE film/Tyvek® film/peelable PE film layers are sealed onto one another in forming the final product package, as a 3-layer bag. The pressurization integrity testing can be accommodated by providing a pressurization gas inlet, such as a spout, gland, or other inlet connector element, attached to the PE film in such manner as to allow ingress of gas therethrough into the interior volume of the container package. The integrity test then is simply carried out by testing the bag for pressure loss when the bag is filled with compressed air. The integrity test can be performed after production (sealing) of the bag or after the filling of the bag with the product article, as necessary or desirable in a given end use application of the invention. After a (successful) integrity test, peelable PE film can be readily peeled off manually, or automatically (e.g., by a suction plate element joined by suitable conduit to a vacuum pump), and the bag can be submitted to steam- and/or EPO-sterilization.

In the foregoing illustrative embodiment employing PE film/Tyvek® film/peelable PE film layers, the sealing parameters are desirably set to seal all three layers against each other resulting in a strong PE/Tyvek® film seal having a seal strength greater than about 20 Newtons/15 millimeters seal width, and a peelable Tyvek® film/peelable PE seal on the order of about 5 Newtons/15 millimeters seal width, e.g., in a range of from about 1 to about 8 Newtons/5 millimeters seal width.

The component layers of multilayer films and packaging sheet thicknesses in the broad practice of the present invention can be readily determined without undue experimentation within the skill of the art, based on the disclosure herein, to provide packaging with appropriate properties for the specific contained product and ultimate use and storage environments of the packaging. In general, the Tyvek® sheets used in the practice of the invention, or alternatively of other porous material sheets, should have a thickness that provides appropriate structural strength and integrity to the packaging, e.g., in a thickness range of from about 25 micrometers to about 3 millimeters, and the peelable layers and non-porous sheets employed in the practice of the invention can for example be of thickness in a corresponding range of thickness values.

It will be recognized that while the invention is illustratively described herein with reference to packaging that includes porous and non-porous sheet materials, the invention is also susceptible of implementation in packaging in which the entire package as ultimately used is formed of a sheet or web material that is porous in character. In such totally porous packaging, the respective walls or sheet portions of the package can be overlaid with peelable films conferring temporary non-porous character to the packaging and allowing the integrity testing of the package or portions thereof. The invention thus has broad applicability, and the illustrative embodiments herein described, having porous and non-porous sheets as structural elements thereof, relate to one form of the invention.

FIG. 1 is a schematic representation of a portion of a package 20 according to one embodiment of the invention, showing the constituent laminae thereof.

The package 20 comprises a porous material layer 26, such as Tyvek® sheet, which is bonded to non-porous sheet 28, e.g., of polyethylene, by fusion bond 14 as shown. The fusion bond 14 can be formed by ultrasonic welding of the sheets 26 and 28 to another at their registered edges, using a Branson ultrasonic welder (Branson Products, Inc., Danbury, Conn.) or other suitable ultrasonic welding tool. The bonded sheets 26 and 28, joined at their edges, thereby define an enclosed interior volume 16 therebetween, for containment of a product article therein, e.g., a medical device or therapeutic agent.

On the exterior face of the porous material layer 26 (the top surface in the view shown), is sealed the peelably removable sheet 18. In the illustrated embodiment, the peelable sheet 18 is of a 2-layer construction, including a first layer 24 of a peelable polymeric film material in facial contact with the porous material sheet 26, and a second layer 22 of a backing material, e.g., polyethylene. The overlying sheet 18 remains in sealing contact with the porous sheet 26 during the pressurization testing of the integrity of the package, and thereafter overlying sheet 18 is peeled away and removed from the porous sheet 26.

Figure 2:
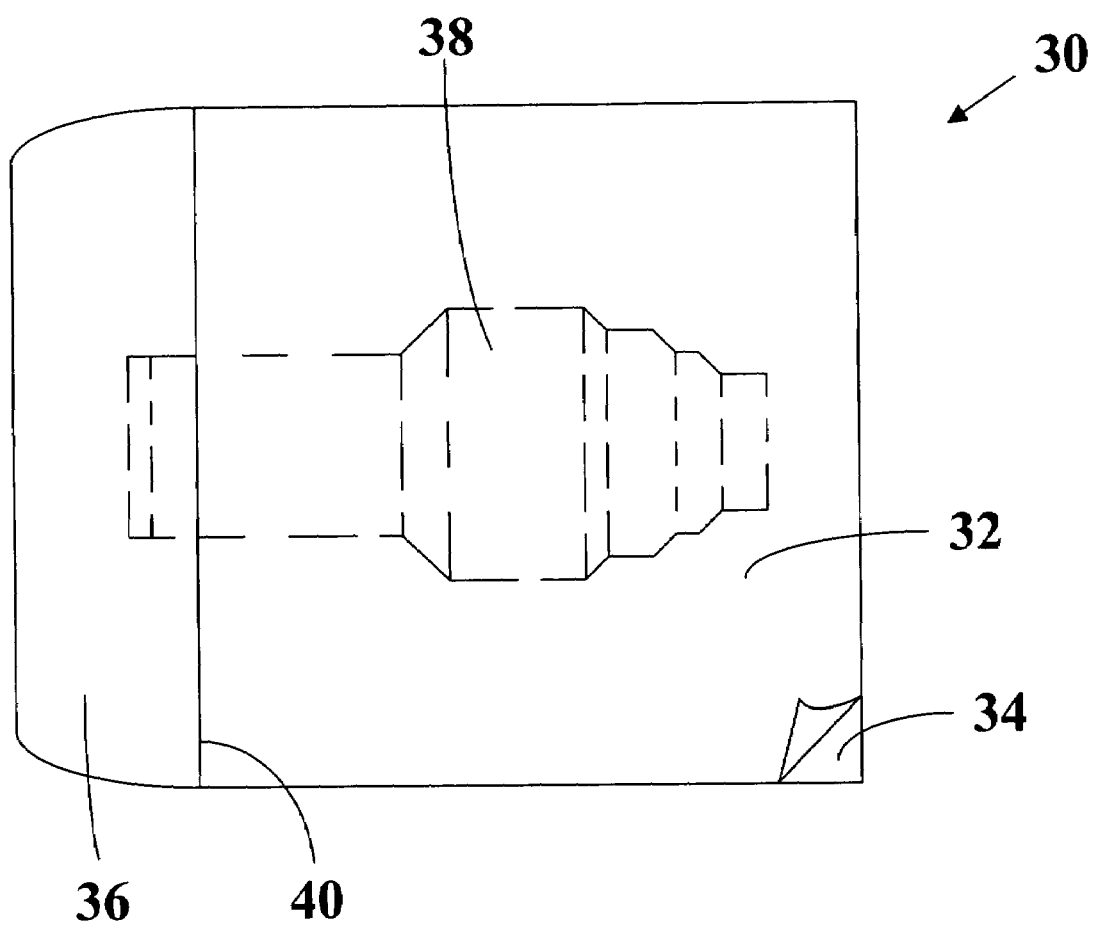
FIG. 2 is a top plan view of a package according to another embodiment of the invention, containing a catheter coupling assembly, as employed for interconnecting a catheter to an angiographic syringe.

FIG. 2 is a top plan view of a package 30 according to another embodiment of the invention, containing a catheter coupling assembly 38, as employed for interconnecting a catheter to an angiographic syringe.

The package 30 comprises a non-porous package member 36 which can be of a tray or cassette form, defining a receptacle within which the catheter coupling assembly is disposed. The non-porous package member 36 has a cover bonded thereto, e.g., along the seam line 40. The cover member comprises a porous material sheet 34 as an underlying element thereof, and an overlying sheet 32, which as shown in the lower right-hand portion of the product package is partially peeled away from the underlying porous material sheet 34. The overlying sheet can be a coextruded sheet formed of a peel layer and a backing layer, as described hereinabove, or the overlying sheet can be a single-layer sheet of a peelable and non-porous material.

It will therefore be seen that the present invention provides a composite film structure that is usefully employed for forming packaging that must be subjected to pressurization integrity testing, and which in subsequent processing must be sufficiently pervious to sterilant gases.

The specific film and sheet materials used in the packaging of the invention can be widely varied in the practice of the invention, as is readily determinable within the skill of the art, based on the disclosure herein. In like manner, the thicknesses of the specific film and sheet materials are widely variable, depending on the integrity test pressure conditions and the ultimate requirements of the product that is contained in the package.

It will therefore be recognized that while the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

What is claimed is:

1. A packaging article, comprising:
   a base member;
   a first sheet of a porous material joined along at least a first edge portion thereof to the base member to define an enclosed interior volume;
   a second sheet overlying and sealed to the first sheet, said second sheet (i) being non-porous to passage of gas therethrough and (ii) comprising a peelable film in facial contact with the first sheet, said peelable film permitting peeling removal of the second sheet from the first sheet to expose the first sheet for passage of gas therethrough; and
   a pressurization gas inlet adapted to permit the ingress of pressurization gas to the enclosed interior volume, the inlet comprising a gland adapted to prevent fluid leakage.

2. The packaging article of claim 1, wherein said first sheet comprises a material selected from the group consisting of cellulosic and synthetic polymeric materials.

3. The packaging article of claim 2, wherein said first sheet comprises a cellulosic material.

4. The packaging article of claim 3, wherein said cellulosic material comprises paper.

5. The packaging article of claim 2, wherein said first sheet comprises a synthetic polymeric material.

6. The packaging article of claim 5, wherein said synthetic polymeric material comprises polyethylene.

7. The packaging article of claim 6, wherein the polyethylene comprises high-density polyethylene.

8. The packaging article of claim 1, wherein said first sheet comprises a flash-spun and bonded polymeric fibrous web.

9. The packaging article of claim 8, wherein said web comprises high density polyethylene fiber.

10. The packaging article of claim 1, wherein said first sheet comprises a porous web of a material selected from the group consisting of polyethylene, polysulfone, polyimide, polypropylene, polybutylene, polyvinylchloride, polyurethane, and polystyrene.

11. The packaging article of claim 1, wherein said first sheet comprises a film of heat- and pressure-consolidated flash-spun high density polyethylene fibers.

12. The packaging article of claim 1, wherein the second sheet further comprises a backing layer secured to the peelable film.

13. The packaging article of claim 1, in the form of a bag adapted to hold a product article therein.

14. The packaging article of claim 1, wherein the packaging article comprises a containment structure for a product article that must be sterile in end usage thereof.

15. The packaging article of claim 14, containing a medical device.

16. The packaging article of claim 14, containing a pharmaceutical agent.

17. The packaging article of claim 1 wherein the pressurization gas inlet is joined to the base member.

18. A packaging article useful for pressurization integrity testing and after pressurization integrity testing being permeable to sterilant gas for sterile packaging of a product article disposable therein, said packaging article comprising:
   a base member;
   a first sheet of a porous material joined along at least a first edge portion thereof to the base member to define an enclosed interior volume, the first sheet being permeable to passage of sterilant gas therethrough in exposure to a sterilant gas environment;
   a second sheet overlying and sealed to the first sheet, said second sheet (i) being non-porous to passage of said sterilant gas therethrough and (ii) comprising a peelable film in facial contact with the first sheet of porous material, said peelable film permitting peeling removal of the second sheet from the first sheet to expose the first sheet for passage of said sterilant gas therethrough; and
   a pressurization gas inlet adapted to permit the ingress of pressurization gas to the enclosed interior volume for pressurization integrity testing, the inlet comprising a gland adapted to prevent fluid leakage.

19. The packaging article of claim 18, wherein said first sheet comprises a cellulosic material.

20. The packaging article of claim 19, wherein said cellulosic material comprises paper.

21. The packaging article of claim 18, wherein said first sheet comprises a synthetic polymeric material.

22. The packaging article of claim 21, wherein said synthetic polymeric material comprises polyethylene.

23. The packaging article of claim 22, wherein the polyethylene comprises high-density polyethylene.

24. The packaging article of claim 18, wherein said first sheet comprises a flash-spun and bonded polymeric fibrous web.

25. The packaging article of claim 24, wherein said web comprises high-density polyethylene fiber.

26. The packaging article of claim 18, wherein said first sheet comprises a porous web of a material selected from the group consisting of polyethylene, polysulfone, polyimide, polypropylene, polybutylene, polyvinylchloride, polyurethane, and polystyrene.

27. The packaging article of claim 18, wherein said first sheet comprises a film of heat- and pressure-consolidated flash-spun high density polyethylene fibers.

28. The packaging article of claim 18, wherein the second sheet further comprises a backing layer secured to the peelable film.

29. The packaging article of claim 18, wherein the base member comprises a non-porous structural component.

30. The packaging article of claim 29, wherein said non-porous structural component is of sheet form.

31. The packaging article of claim 29, wherein said non-porous structural component comprises a shaped member adapted to secure at least a portion of said product article therein.

32. The packaging article of claim 18, in the form of a bag adapted to hold said product article therein.

33. The packaging article of claim 32, wherein said first sheet comprises a non-porous polyethylene sheet.

34. The packaging article of claim 33, wherein said first sheet comprises a film of heat- and pressure-consolidated flash-spun high density fibers.

35. The packaging article of claim 18, having a product article packaged therein.

36. The packaging article of claim 35, wherein said product article must be sterile in end usage thereof.

37. The packaging article of claim 36, wherein said product article comprises a medical device.

38. The packaging article of claim 36, wherein the product article comprises a pharmaceutical agent.

39. The packaging article of claim 18, in the form of a bag, wherein the base member comprises a non-porous panel, and wherein said first sheet comprises a film of heat- and pressure-consolidated flash-spun high density polyethylene fibers, and said non-porous panel is formed of polyethylene film.

40. The packaging article of claim 39, wherein the first sheet is joined to the base member at a bonded edge region having a bond strength greater than about 20 Newtons per 15 millimeter bonded edge region width.

41. The packaging article of claim 40, wherein the second sheet is sealed to the first sheet with a seal strength in a range of from about 1 to about 8 Newtons per 15 millimeters seal width.

42. The packaging article of claim 18 wherein the pressurization gas inlet is joined to the base member.

* * * * *